United States Patent [19]

Dryden, Jr. et al.

[11] 4,141,920
[45] Feb. 27, 1979

[54] PROCESS FOR THE PREPARATION OF TRIMETHYLSULFOXONIUM BROMIDE

[75] Inventors: Hugh L. Dryden, Jr., Deerfield; Mike G. Scaros, Arlington Heights, both of Ill.; John P. Westrich, Racine, Wis.

[73] Assignee: G. D. Searle & Co., Chicago, Ill.

[21] Appl. No.: 831,726

[22] Filed: Sep. 9, 1977

[51] Int. Cl.$^2$ ............................................ C07C 148/00
[52] U.S. Cl. ................................................. 260/607 B
[58] Field of Search ........................ 260/607 R, 607 B

[56] References Cited

PUBLICATIONS

Justus Liebig's Annalen, 611, pp. 117–121 (1958).
Tetrahedron Letters, No. 6, pp. 467–470, (1969), (Dusseau et al.).
Berichte, 62B, pp. 2844–2850 (1929).
Chemical Abstracts, 22, 1756 (B. V. Ironov et al.) (1928).
J. American Chem. Soc., 85, 3264–3268 (R. H. DeWolffe et al.) (1963).
J. American Chem. Soc., 87:4593–4596 (1965), (A. J. Krege et al.).
Inorg. Nucl. Lett., 5, 639 (1969), (Blaschette et al.).
Chem. Eng. News, 51 (51), 37 (1973), (Scaros & Serauskas).
Chem. Brit., 9 (11), 523 (1973), (Scaros & Serauskas).

*Primary Examiner*—Elbert L. Roberts
*Assistant Examiner*—Molly C. Eakin

[57] ABSTRACT

The present invention is concerned with an improved process for the preparation of trimethylsulfoxonium bromide. The improvement in the process comprises the addition of a scavenger to the reaction mixture of dimethyl sulfoxide and methyl bromide.

5 Claims, No Drawings

PROCESS FOR THE PREPARATION OF TRIMETHYLSULFOXONIUM BROMIDE

The present invention concerns an improved process for the preparation of trimethylsulfoxonium bromide. The improvement in the process comprises the addition of a scavenger selected from the group consisting of trimethyl orthoformate, triethyl orthoformate and tetramethyl orthocarbonate to the reaction mixture of dimethylsulfoxide and methyl bromide.

Trimethylsulfoxonium bromide is described by Blaschette and Buerger, *Inorg. Nucl. Lett.*, 5, 639 (1969). The compound is useful as an intermediate in the preparation of potassium 6$\beta$,7$\beta$-dihydro-17-hydroxy-3-oxo-3'H-cyclopropa [6,7]-17$\alpha$-pregn-4-ene-21-carboxylate which is described in the literature as a potent and selective diuretic agent.

The reaction of alkyl halides with sulfoxide compounds is described in the article by Kuhn and Trischmann, *Ann.*, 611, 117 (1958). More particularly, the article describes preparation of trimethylsulfoxonium iodide by heating for several days a mixture of dimethyl sulfoxide and methyl iodide. No violent reaction has been reported in connection with this reaction.

However, in the course of a synthesis of trimethylsulfoxonium bromide, by heating at about 66° C. a mixture of dimethylsulfoxide and methyl bromide the violent reaction and explosion of the reaction vessel has been reported in the literature (see Mike G. Scaros and Joy A. Serauskas, *Chem. Eng. News*, 51 (51), 37 (1973) and *Chem. Brit.*, 9 (11), 523 (1973). The hazards of the violent reaction and explosion have been attributed to the presence of bromine and hydrogen bromide as the by-products in the reaction mixture. These two ingredients appear to catalyze the rapid exothermic decomposition of the reaction mixture leading to the formation of gaseous products and the buildup of gas pressure which causes the reaction vessel to explode. Because of inherent hazards the reaction of dimethylsulfoxide and methyl bromide is customarily carried out in a barricaded area equipped with the proper equipment to control any possible decomposition. The pressure is carefully monitored and plotted on a chart with respect to time; if a break in the normal pressure time curve occurs (indicating a pressure buildup due to the gaseous decomposition products) the reaction is stopped at once. The hazards involved in this reaction may also be reduced by decreasing the reaction time to less than 50 hours. However, this may not be suitable because yields of trimethylsulfoxonium bromide will also be reduced.

It is an object of the present invention to avoid hazards described above and to provide simpler and safer procedure for the preparation of trimethylsulfoxonium bromide with little, if any, loss in the desired product.

According to the present invention, the reaction of dimethylsulfoxide and methyl bromide is carried out in the presence of a scavenger such as trimethyl orthoformate, triethyl orthoformate and tetramethyl orthocarbonate. The reaction is conveniently carried out at a temperature of about 20°–80° C., preferably at about 60°–65° C. When the reaction is carried out at 60°–65° C. for 48–55 hours it provides a yield of about 80%. When the reaction is carried out at about 25° C. for four to five weeks it provides a yield of about 50%.

It is believed that the scavenger reacts with the bromine and hydrogen bromide by-products and, thus, prevents the possible exothermic decomposition of the mixture. The role of trimethyl orthoformate as the scavenger can be shown by the following scheme.

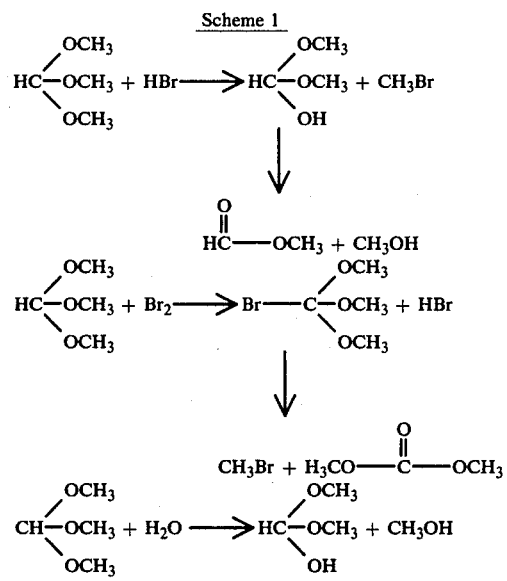

Scheme 1

The effectiveness of the scavengers in keeping the quantity of bromine and hydrogen bromide low, the two ingredients which appear to catalyze the rapid decomposition of the reaction mixture is shown in Table 1, on the next page.

Tetramethyl orthocarbonate is the preferred scavenger. The most preferred scavenger is trimethyl orthoformate.

The reaction temperature is not critical. However, the yields are better and the reaction time is shorter when the reaction is carried out at a temperature of 20°–80° C. The preferred temperature is 60°–65° C. The reaction will proceed both at temperatures lower than 20° C. and higher than 80° C. However, it may not be suitable to run the reaction at a temperature lower than 20° C. because of low yields and long reaction time. It is also not practical to carry out the reaction at a temperature higher than 80° C. due to the increased risks of exothermic decomposition of the reaction mixture.

The ratio of scavenger used is not critical, although the best results are achieved by using 10% molar ratio of a scavenger to dimethyl sulfoxide.

The following Examples are given to further illustrate the present invention. They should not be construed as limiting the invention either in spirit or in scope.

Table 1

| Scavenger | Time | Temperature | Br$_2$ Concentration | H$^\oplus$ Concentration |
|---|---|---|---|---|
| Trimethyl Orthoformate | 48 hours | 60° C. | 0.4667 mg/ml | 0.025 molar |
| Triethyl Orthoformate | 48 hours | 60° C. | 0.5799 mg/ml | 0.053 molar |
| Tetramethyl Orthocarbonate | 48 hours | 60° C. | 0.2263 mg/ml | 0.0137 molar |
| None | 48 hours | 60° C. | 2.90 mg/ml | 0.15 molar |
| Trimethyl Orthoformate | 28 days | 25° C. | 1.5982 mg/ml | 0.027 molar |

Table 1-continued

| Scavenger | Time | Temperature | $Br_2$ Concentration | $H^{\oplus}$ Concentration |
|---|---|---|---|---|
| None | 28 days | 25° C. | 3.90 mg/ml | 0.15 molar |

EXAMPLE 1

A 20 liter glass carboy is charged with 10 l. of dimethyl sulfoxide and 300 ml. of trimethyl orthoformate and to this mixture is added, using adequate ventilation, 3 l. of methyl bromide with stirring. The carboy is stoppered and connected to a gas trap filled with dimethyl sulfoxide. The gas trap serves to relieve any pressure within the carboy and scrub any methyl bromide that escapes. This mixture is left to react for about 28 days at room temperature. At the end of this time, crystals formed in the carboy. The crystals are removed by filtration, washed with 3 l. of isopropanol, and air dried at 100° C. for about 18 hours to give crude trimethylsulfoxonium bromide in about 55% yield.

A mixture of 5 kg. of crude trimethylsulfoxonium bromide, 250 gr. of Darco brand of activated carbon, grade G-60, sold by Chemical Division of Atlas Chemical Industries, Inc. and 4 l. of water is heated in a 10-gallon stainless steel kettle to 70° C. for about 15 minutes. The resulting warm solution is filtered through Celite brand of diatomaceous earth sold by Johns-Manville Corporation to remove Darco brand of activated carbon, grade G-60, sold by Chemical Division of Atlas Chemical Industries, Inc. and the filtrate is collected. The kettle and Darco brand of activated carbon, grade G-60, sold by Chemical Division of Atlas Chemical Industries, Inc. on filter are washed with a total of 1 l. of 65°-75° C. warm water. The solutions are combined, and the combined solution is stirred and cooled to a temperature of 0°-10° C. Then, 20 l. of isopropanol is added over 15 minute period and the resulting mixture is stirred at 0°-10° C. for 2-3 hours. The white crystals of pure trimethylsulfoxonium bromide which formed are separated by filtration, washed with 5 l. of cold (0°-10° C.) isopropanol and air dried at about 100° C. for about 18 hours. The product is recovered in about 90% yield.

EXAMPLE 2

A 2-liter glass pressure vessel (tested to 120 psi) is charged with 900 ml. of dimethyl sulfoxide and 35 ml. trimethyl orthoformate and, then, 350 ml. of methyl bromide is added with adequate ventilation while the mixture is stirred. After the addition of methyl bromide is completed the reaction bottle is stoppered with a Teflon stopper equipped with a pressure gauge, vent valve and thermocouple, and heated at a temperature of 65° C. for 55 hours in a glycol bath. A thermo-watch is used to control temperature during this time. At the end of 55 hours heating is discontinued, the reaction bottle cooled to room temperature and vented through the vent valve. The crystals which formed in the reaction are separated by filtration, washed with 2 l. of benzene and dried in vacuum oven at 50° C. for about two hours to afford trimethylsulfoxonium bromide in about 80% yield.

EXAMPLE 3

When an equivalent quantity of tetramethyl orthocarbonate is substituted for trimethyl orthoformate called for in Example 2, and the procedure detailed therein substantially repeated, trimethylsulfoxonium bromide is obtained in approximately the same yield.

EXAMPLE 4

When an equivalent quantity of triethyl orthoformate is substituted for trimethyl orthoformate called for in Example 2 and the procedure detailed therein substantially repeated, there is obtained triethylsulfoxonium bromide in about the same yield.

What we claim is:

1. In a process for the preparation of trimethylsulfoxonium bromide by reacting dimethylsulfoxide with methyl bromide, the improvement comprising the addition of a scavenger selected from the group consisting of trimethyl orthoformate, triethyl orthoformate and tetramethyl orthocarbonate to the reaction mixture.

2. A process for the preparation of trimethylsulfoxonium bromide which comprises reacting dimethylsulfoxide with methyl bromide in the presence of a scavenger selected from the group consisting of trimethyl orthoformate, triethyl orthoformate and tetramethyl orthocarbonate at a temperature of 20°-80° C.

3. A process according to claim 2, wherein the molar ratio of the scavenger to dimethylsulfoxide is 10%.

4. A process according to claim 2, wherein trimethyl orthoformate is used as the scavenger.

5. A process according to claim 2 which is carried out at a temperature of 60°-65° C.

* * * * *